United States Patent

Aubert et al.

[11] Patent Number: 5,266,013
[45] Date of Patent: Nov. 30, 1993

[54] PORTABLE PUMP FOR THE ADMINISTRATION OF A THERAPEUTIC

[75] Inventors: Christophe Aubert, Fontainemelon, Switzerland; Antoine Dubois, Villers-le-Lac, France

[73] Assignee: Asulab S.A., Bienne, Switzerland

[21] Appl. No.: 675,094

[22] Filed: Mar. 25, 1991

[30] Foreign Application Priority Data

Mar. 23, 1990 [FR] France ................... 90 03869

[51] Int. Cl.$^5$ .................... F04B 43/12; F04B 39/14
[52] U.S. Cl. ............................ 417/474; 417/477; 417/360; 604/153
[58] Field of Search .................... 604/151, 153; 417/474–477, 163, 360

[56] References Cited

U.S. PATENT DOCUMENTS

| | | | |
|---|---|---|---|
| 4,187,057 | 2/1980 | Xanthopoulos | 417/477 |
| 4,211,519 | 7/1980 | Hogan | 417/477 |
| 4,473,342 | 9/1984 | Iles | 417/360 |
| 4,498,843 | 2/1985 | Schneider | 417/22 |
| 4,653,987 | 3/1987 | Tsuji | 417/360 |
| 4,735,558 | 4/1988 | Keinholz | 417/477 |
| 4,755,109 | 7/1988 | Botts | 417/360 |
| 4,818,190 | 4/1989 | Pelmulder | 417/360 |
| 4,872,813 | 10/1989 | Gorton | 417/360 |
| 4,930,997 | 6/1990 | Bennett | 417/410 |
| 4,976,590 | 12/1990 | Baldwin | 417/777 |
| 5,011,378 | 4/1991 | Brown | 417/360 |
| 5,609,641 | 7/1991 | Gorton | 417/360 |

FOREIGN PATENT DOCUMENTS

| | | |
|---|---|---|
| 0275213 | 7/1988 | European Pat. Off. . |
| 0275214 | 7/1988 | European Pat. Off. . |
| 2632529 | 6/1988 | France . |
| 2120003 | 11/1983 | United Kingdom . |

*Primary Examiner*—Richard A. Bertsch
*Assistant Examiner*—Peter Korytnyk
*Attorney, Agent, or Firm*—Weil, Gotshal & Manges

[57] ABSTRACT

A portable pump for the administration of a therapeutic liquid substance having at least one integral supply reservoir is disclosed. The object of the invention is to present a pump having at least two modules in which the sterilizable elements are divided from the non-sterilizable elements, the operation of the pump being started when the various modules are assembled and being permanently disrupted when the modules are separated. The object of the invention is achieved with the aid of a pump comprising a reservoir module having a supply reservoir of medicaments and at least one tube connected to the reservoir at the end of the pump, and a motor module comprising means for pumping motor means and control means. This pump is particularly useful for the treatment of patients in continuous low doses.

22 Claims, 7 Drawing Sheets

Fig. 12

PORTABLE PUMP FOR THE ADMINISTRATION OF A THERAPEUTIC

FIELD OF THE INVENTION

The present invention relates to a portable pump having an integral reservoir enabling the administration of a therapeutic liquid substance Medical pumps permitting the administration to a patient of medicaments in liquid form have been known for at least a decade. This type of pump is of particular use for example in the treatment of diabetics, cancer patients and AIDS patients, who need to receive medicaments continuously in small doses, without it being necessary to confine them to bed and equip them with a cumbersome medical apparatus. These pumps have small dimensions so that they are autonomous for several days permitting the patient to move about freely. It is merely necessary to refill the reservoir at regular intervals.

In the medical field peristaltic pumps are frequently used.

DESCRIPTION OF THE PRIOR ART

International Patent Application No. WO 82/04291 describes a peristaltic pump which functions according to a well-known principal. It comprises the use of a tube of plastic deformable material which is then squeezed at one point against a casing by means of a rotor having pressure rollers, the rotor being moved in a rotary manner by a rotor in order to aspirate liquid contained in the tube and coming from a reservoir and then to force it towards the pump exit.

French Patent No. FR 8904044 in the name of the applicants also describes a pump of this type which is useful in the medical field. This pump comprises what may be described as a "pump unit", supplied by a flexible tube from an independent reservoir in the form of a bag of flexible plastic material. This pump unit has two modules, a motor module which is non sterilizable comprising a motor and its control circuit and a pump module which is sterilizable, comprising a rotor equipped with contact rollers, a tube and a pressure cylinder which cooperates with the contact rollers to squeeze the said tube. These two modules can be assembled and dismantled at will.

This pump having two dismantlable parts is already known and may be easily sterilized since it is manufactured in such a way that the component parts which do not withstand sterilization are situated in only one of the parts.

However, this pump does not have the desired safety factor since the user himself can have access to its mechanism and to its reservoir since the two parts can be easily dismantled.

This inconvenience is further aggravated in that the pump is equipped with a control switch to start and stop the operation and which is also accessible to the user. The user can thus very easily employ the pump for uses other than the treatment envisaged by the doctor.

OBJECTS OF THE INVENTION

It is an object of the present invention to overcome the disadvantages mentioned above.

BRIEF SUMMARY OF THE INVENTION

It is thus an object of the present invention to provide a portable pump for the administration of a therapeutic liquid substance comprising the following features:
  a supply reservoir for the said substance
  pumping means permitting provision of the said therapeutic substance from the supply reservoir up to the pump exit
  motor means for setting into operation the said pump means
  control means for the said motor means
said features being disposed in a plurality of assembled modules characterized in that at least two of the said modules comprise matching electrical contact means setting into operation the functioning of the pump following assembly of the modules and means for permanently disrupting functioning of the pump when the electrical contacts are disassembled.

BRIEF DESCRIPTION OF THE INVENTION

Due to these characteristics and owing to the easy sterilizability the pump according to the invention shows all the desirable safety guarantees since,
  once assembled, functioning the pump is started simply by the assembly operations,
  once assembled it is not possible to dismantle the device except at the price of destroying one or more of the elements essential to its structure, in particular the control circuit for the pump, which cannot be repaired by the user, being an unskilled person.

According to a particularly advantageous characteristic of the invention the permanent disruption means are made up of mechanical elements carrying the electrical contacts and means for their destruction in a permanent manner when the modules are disassembled.

Thanks to these characteristics not only is the pump automatically put into operation when the modules are assembled but any possible disassembly thereof results in breaking of the supports of the electrical contacts. It is thus difficult to put the pump into operation again, since it is necessary to reassemble the broken pieces and then to reconstruct them in the interior of the device.

According to a further characteristic of the invention the permanent disruption means are placed in a control circuit.

One can thus ensure in a reliable manner that reuse of the pump is impossible since the electronic control means are rendered permanently inoperable when the modules are separated. It is in effect practically impossible for a non-skilled user to reconstruct the electronic circuit again.

Furthermore according to another characteristic of the invention the assembled modules comprise a supply reservoir and this reservoir has a filling inlet disposed in a manner such that it is inaccessible when the module is assembled with the other modules.

In this manner, easy access to the supply reservoir is prevented.

Furthermore, according to a further characteristic of the invention the reservoir module is sterilizable before non-dismantlable assembly with the other modules. One can thus selectively sterilize the module containing the reservoir and does not have to sterilize the module(s) containing the motor and the control circuit since sterilisation techniques often destroy electronic circuits. Furthermore, this pump comprises sealing means capable of sealing the pump, once the two modules are assembled. This permits the user to keep the pump with him in complete security and for example to bathe while carrying the said pump. Preferably, this pump has two modules; a reservoir module containing the medicament reservoir and the tube(s) leading from the reservoir to the pump exit and a motor module comprising the motor means, the control means and a rotor.

The two modules are thus supplied separately and only assembled at the moment of utilization of the pump so that during the storage time the tubes are not deformed or squeezed by the rotor.

BRIEF DESCRIPTION OF THE DRAWINGS

The invention will now be further and better described according to the teachings of the following description by way of example and with particular reference to the accompanying drawings in which:

FIG. 3 is a top plan view of a pump according to FIG. 2 with the two modules in the assembled position and the upper casing of the pump having been removed.

DETAILED DESCRIPTION OF THE INVENTION

Figure 1:
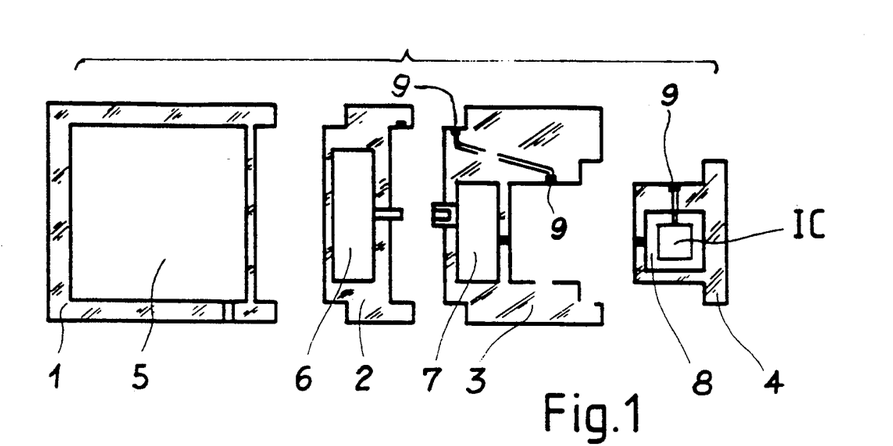
FIG. 1 is a diagrammatic view of the principle of the invention.

The invention is based on the principle of which one variation is shown schematically in FIG. 1. All the elements making up the apparatus of the invention are portrayed in this figure but do not show in any way the exact structure of the said apparatus. Specific constructions are on the other hand shown in the subsequent figures.

As illustrated in FIG. 1 the pump is made up of at least two modules, in this case four, indicated by reference numerals 1, 2, 3 and 4, assembled the one with the others. In a preferred embodiment according to the invention the modules are assembled by sliding one of the modules into the other and held together by a latch mechanism but it is possible to envisage other means such as a threaded joint or the utilisation of a bayonet system or some other means.

The various modules respectively contain several elements, that is to say: a supply reservoir 5 of the therapeutic substance, pump means 6 permitting the said therapeutic substance to be conducted from the reservoir 5 to the pump exit, motor means 7 for putting into operation the said pump means and control means 8 acting on the said motor means 7. The reservoir 5, the pump means 6, the motor means 7 and the control means 8 have been separated and arbitrarily represented in the modules 1 to 4 but it is of course quite clear that the number of modules may be varied and the various elements may be divided differently between the modules. It is, however, advantageous to separate in one or more modules those component parts which do not tolerate sterilisation in order to enable this operation to be carried out on the other modules without damaging the former.

Furthermore at least two of the modules 1, 2, 3 or 4 which simultaneously possess matching electrical contact means 9 enabling the pump to be started when the modules are assembled and causing permanently disconnection of the functioning of the pump when the contact means are subsequently disassembled Preferably, the pump means 6, the motor means 7 and the control means 8 are disposed in the module containing the contact means 9.

The permanent disconnection means are only shown partially and schematically in FIG. 1. According to the invention, they may be put into practice in at least three different ways which may in addition be combined with each other as is the case in one preferred embodiment of the invention which will be described hereinafter.

The first variation may be put into practice by creating an integrated circuit IC which is preprogrammed so that it stops working as soon as the electrical contacts 9, to which it is connected in a special manner, are disconnected, this cessation of working being thus rendered permanent by the programme created in the circuit.

The second variation may be put into practice by providing supports (not shown in FIG. 1) for the electrical contact means 9, these supports being weakened and fashioned in such a manner that they fracture when the modules are disassembled.

The third variation may be put into practice by providing electrical contact means for example on a first module and mechanical means (not shown in FIG. 1) on a second module capable of being assembled with the first, these mechanical means being disposed in such a manner that they break the said electrical contact means 9 when the said modules are disassembled.

It may be noted that in one variation if the module 4 does not contain any element it takes the form of a disconnecting device for the permanent disconnection of the pump.

Figure 2:
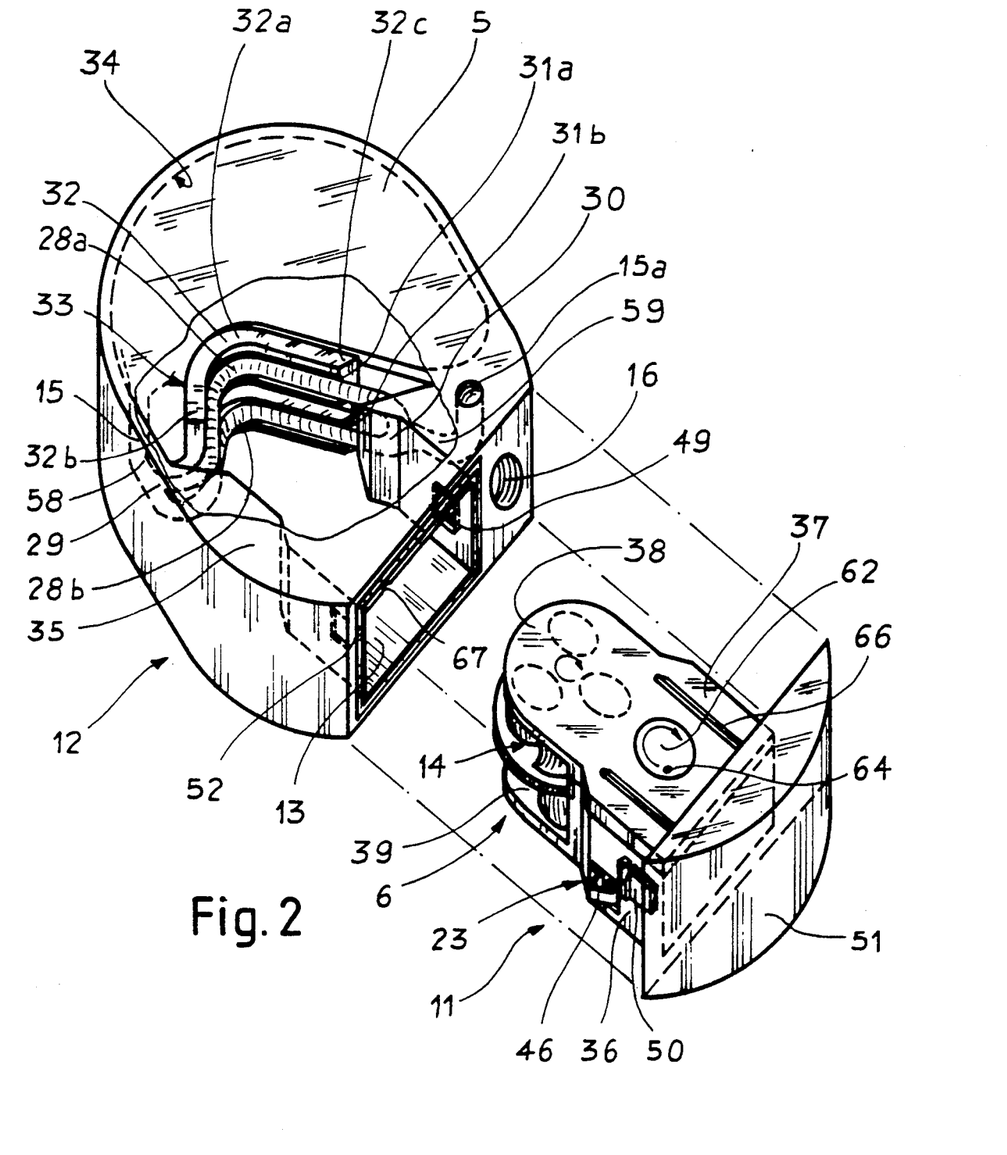
FIG. 2 is a perspective view of a pump before assembly of the two modules.

FIG. 2 shows a pump according to a preferred embodiment of the invention. This pump only contains two modules, that is to say a motor module 11 and a supply module 12. The two modules are adapted to be assembled together. To this end the reservoir module 12 takes the general form of a box equipped with a discharge cavity 13 and the motor module 11 is in the form of a slide member which is adapted to be engaged in the cavity 13 and takes the form substantially complementary thereto.

In this mode of putting the invention into practice the pump means 6 may comprise a peristaltic pump but it is possible to conceive other pump means without going outside the scope of the invention If the pump means comprise a peristaltic pump, the motor module 11 comprises a rotor 14 having two levels of pressure rollers, this rotor being driven by the motor means 7 (not shown in FIG. 2).

The reservoir module 12 comprises a liquid reservoir 5 equipped with a flexible tube 15 which leads to the outlet 15a of the pump. This outlet 15a may for example be connected to a hypodermic needle (not shown) either directly or by way of a flexible tube (also not shown) according to whether the pump is connected for example either to the thorax or the abdomen.

Furthermore the reservoir 5 may be filled by way of a filler opening 16 which preferably takes the form of a septum. As a general idea the assembled pump may have a total length of 55 mm and a total width of 47 mm and a thickness of 14 mm, these dimensions of course only being given by way of example.

The pump will now be described in more detail as follows.

As shown in FIG. 2 the motor module 11 is in elongated form and contains in its narrower portion the rotor 14 and in its wider back portion the motor 7 and the control means 8 (not shown in this figure).

Figure 4:
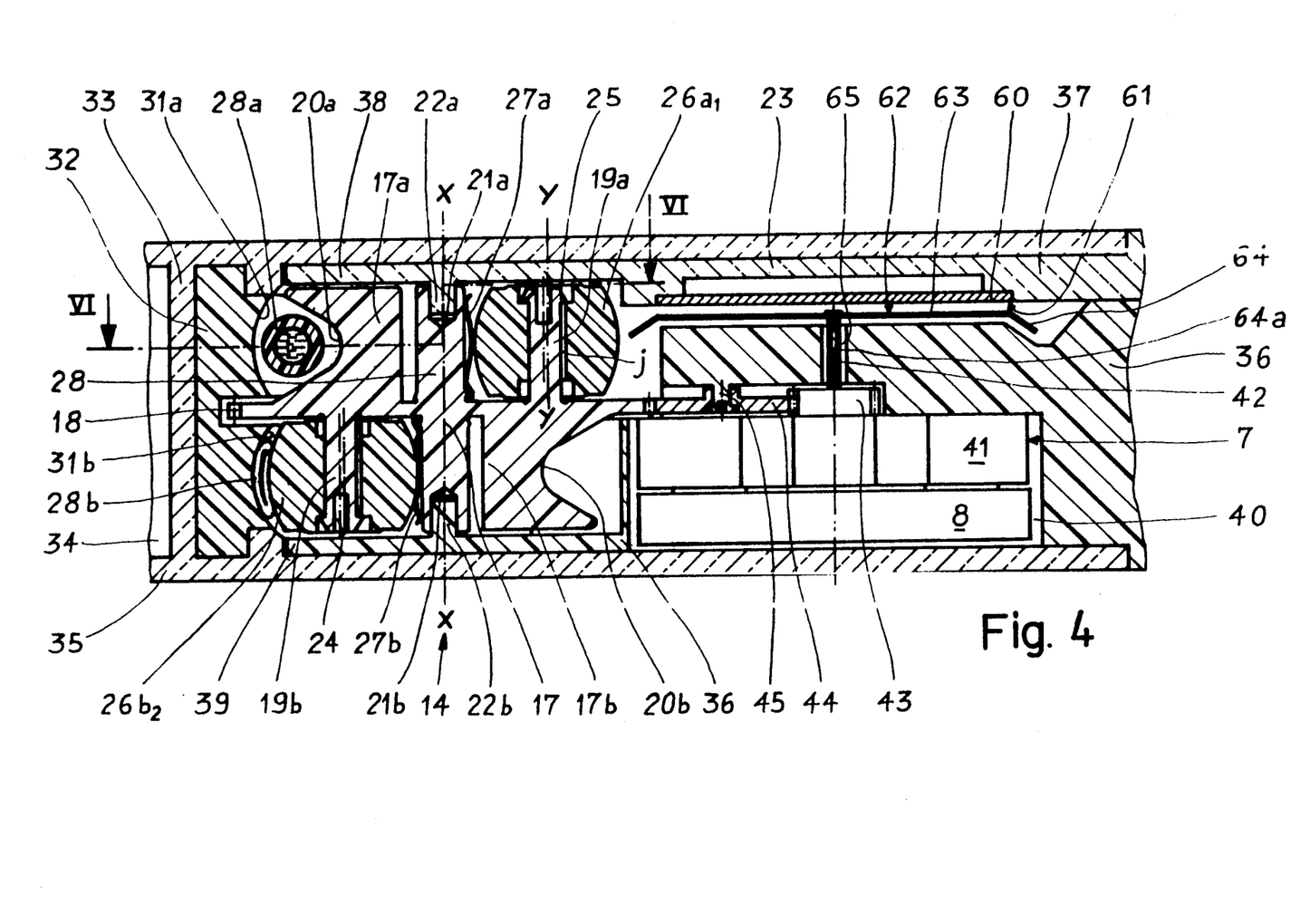
FIG. 4 is a sectional view of a pump along the lines IV—IV of FIG. 3.

As can be seen from FIG. 4 the rotor 14 comprises a body 17 formed in one piece and having a generally cylindrical form whereby the axis X—X is also the axis of rotation. This body 17 defines two layers 17a and 17b situated on each side of the median radial plane in which is provided a toothed gear 18 adapted to ensure the drive and rotation of the said motor. This gear extends across the whole of the cylindrical body which thus has its greatest diameter at this point.

For each level 17a, 17b of the body 17 there are provided X—X. These spindles 19a and 19b are spaced 120° apart from each other and the spindles 19a are spaced 60° apart with respect to the spindles 19b of the lower level (see FIG. 6).

Furthermore for each level 17a, 17b the body 17 has three throats 20a, 20b pointing towards the side surface and taking essentially the form of a V with a rounded end.

Centered on its axis X—X the body 17 also has two blind holes 21a, 21b in which are engaged the pivots 22a and 22b forming part of the block 23 which comprises the supporting structure for the motor means 11.

Each hole 21a, 21b has a radial slit 24 at its free extremity and has at this point an annular rebate 25 forming a shoulder directed towards the base of each pin.

The rotor 14 is equipped on each level with three rollers 26a-1, 26a-2 and 26a-3 as well as 26b-1, 26b-2 and 26b-3 (see FIG. 6) engaging in the respective spindles 19a, 19b and being held in place by a ratchet mechanism against the shoulder 25 always being able to turn freely against the spindles. A slight radial play j is envisaged in order to allow a certain lateral movement of the rollers.

Figure 6:
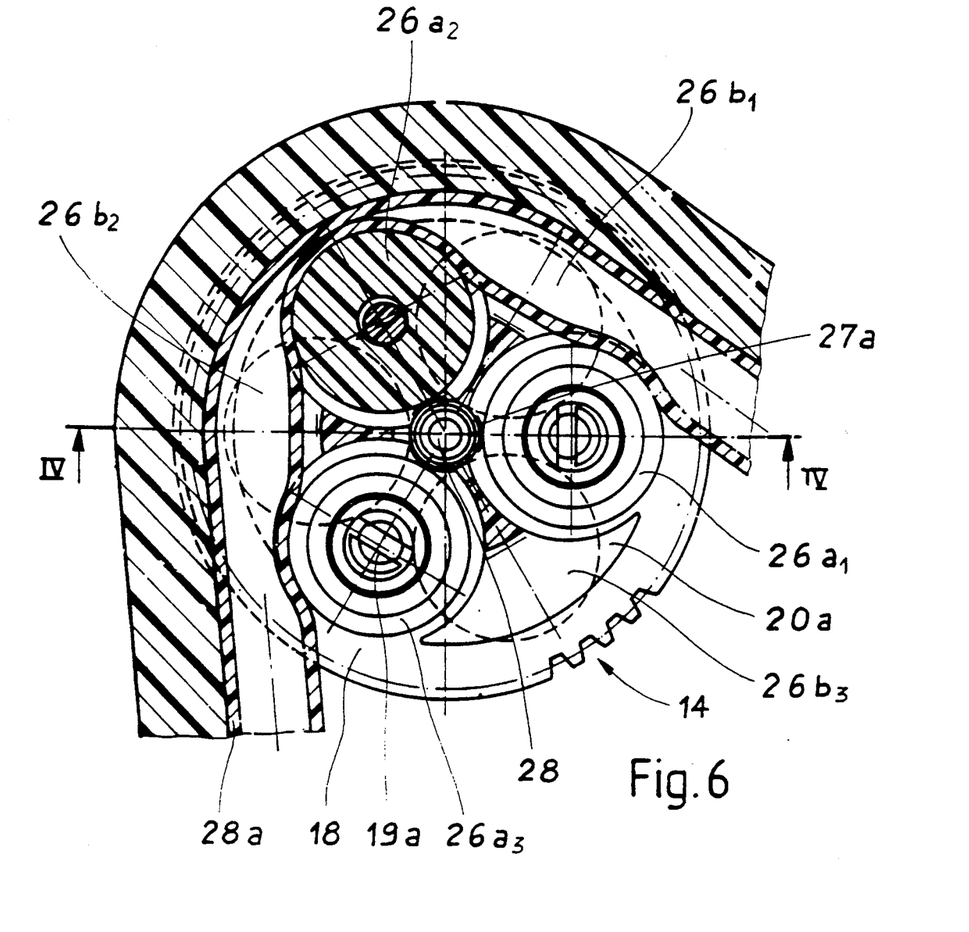
FIG. 6 is a partial sectional view along the lines VI—VI of FIG. 4, FIGS. 7, 8 and 9 are magnified detailed views of FIG. 3 of those parts of the pump indicated respectively by the letters A, B and C.

It should be noted that each throat 20a, 20b is situated between two rollers 26a, 26b adjacent to the same level of the rotor 14.

The leaf springs 27a, 27b are situated in the spaces defined between the rollers 26a, 26b and the central part 28 of the rotor to urge the roller in an outwards direction.

According to a variation of the invention, which is not shown, the individual leaf springs 27a, 27b may be replaced by solid elastomeric blocks one for each level in order to achieve the same effect. Another variation would be to omit them completely, the rollers 26a and 26b being then urged in a radial direction by the inherent elasticity of the tube 15 itself.

Referring once more to FIG. 2 it may be seen that the tube 15 in the present example has two levels of rollers, two tubular elements 28a and 28b one for each level and passes around part of the periphery of the rotor 14 when the modules 11 and 12 are assembled. The tubes 28a, 28b are joined at their corresponding extremities with the Y connectors 29 and 30, the joint 29 being branched towards the supply reservoir 5 (aspiration side of the pump), whereas the joint 30 is in communication with the exit 15 (pump supply side).

The pipes 28a and 28b are situated respectively in the grooves 31a, 31b disposed in the bearing member 32 in the form of a boomerang, abutting against the internal partition 33 separating the compartment 34 of the casing 35 of the reservoir module of the cavity 13 of the latter in which is inserted the motor module 11. The compartment 34 contains the reservoir 5 itself which will be described hereinafter.

Figure 5:
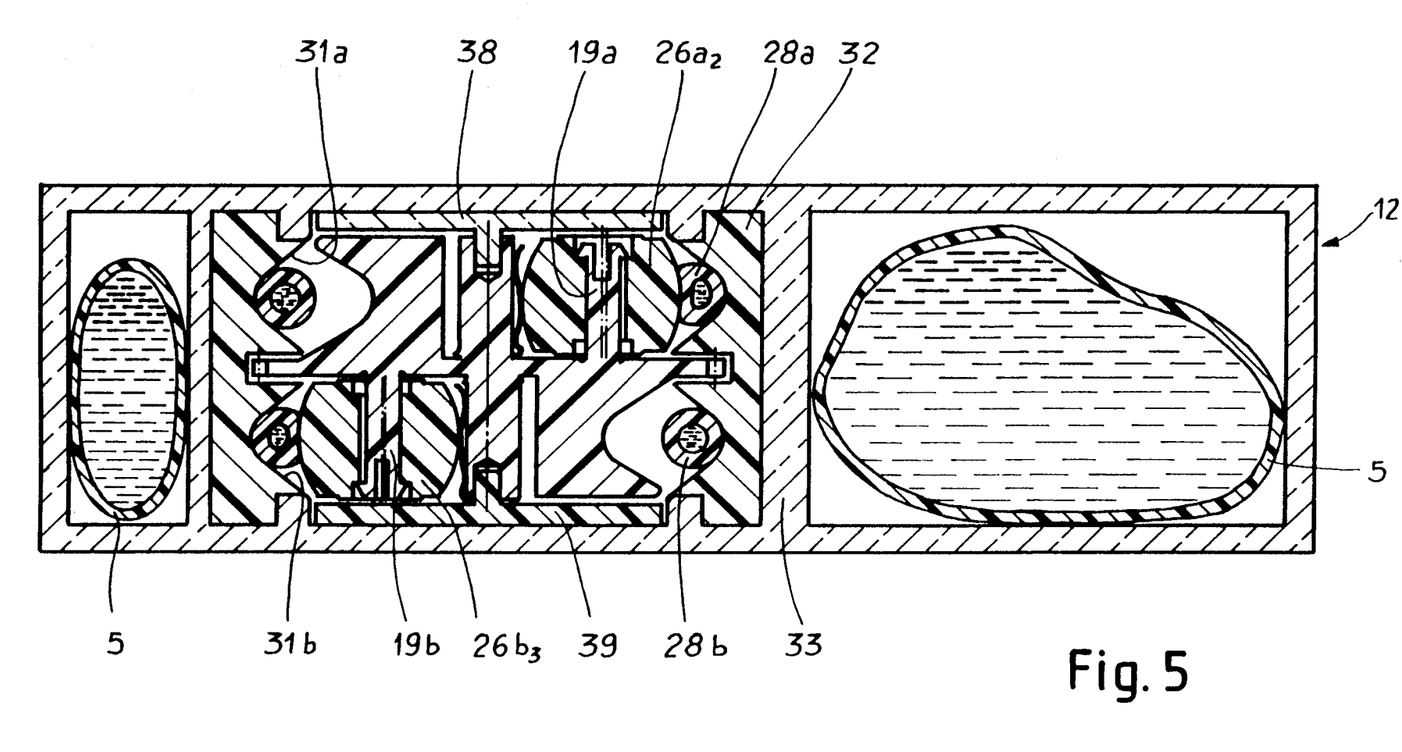
FIG. 5 is a sectional view along the lines V—V of FIG. 3.

As may be seen by comparing the sectional views given in FIGS. 4 and 5 the contour of the grooves 31a and 31b is not constant, their concavity becomes gradually more pronounced as one proceeds from the apex 32a of the bearing towards the extremities 32b and 32c thereof (FIG. 2).

In any case, in a further variation which is not shown the profile of the grooves 31a and 31b is rectilinear and the rollers 26a-1, 26a-2, 26a-3, 26b-1, 26b-2 and 26b-3 are cylindrical. The pipes 28a and 28b are then squeezed between two parallel plains.

The block 23 which forms the structure carrying the motor module 11 comprises a body 36 and a cover plate 37 of transparent material, with projecting portions 38 and 39 in the form of disks projecting from the body and the cover plate comprising a cover for the mounting of the rotor 14. It will be recalled that the latter is mounted rotatively between the pivots 22a and 22b formed out of the same material as the disks 38 and 39.

As shown in FIG. 4 the body 36 is provided with a cavity 40 which serves to hold the motor means 7 and the control system 8. The motor means comprise a drive motor 41 whereby the drive shaft 42 has a pinion 43 engaging with the intermediate wheel 44 mounted rotatably on a bearing 45 situated at the base of the cavity 40. The wheel 44 in its turn engages with the crown pinion 18 of the rotor 14.

Figure 10:
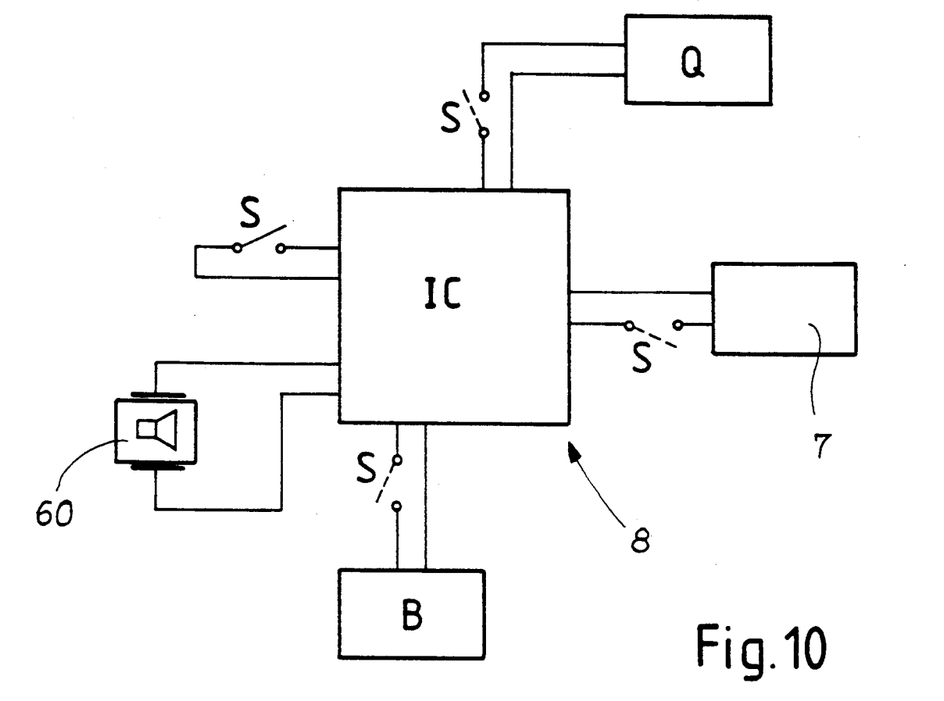
FIG. 10 is a block circuit diagram of the control means for the motor of the pump.

The motor means 7 and the control system 8 may be constructed in the same way as the movements of a conventional watch whereby the axis of the hour hand is the drive shaft 42. Its integrated circuit, normally in conjunction with a quartz crystal, controls the rotation of the hand and is adapted for use with the pump according to the invention. This movement may thus simply be modified so that the integrated circuit may be specifically programmed to control the pump. An example of a watch movement which may be used for this purpose is the Model 400 made and sold by ETA SA, Fabrique des boges, Grange, Switzerland. In FIG. 10 there is shown an electrical block diagram of such a watch movement showing the control means 8 comprising the integrated circuit IC connected on the one hand to the quartz crystal Q and on the other hand to a battery B.

According to the invention the electrical contact means 9 take the form of a switch S connected to two of the input terminals of the integrated circuit. Within the framework of this embodiment of the invention it should be noted that when the switch S is closed for the first time it disconnects the functioning of the integrated circuit IC in order to start the motor means 7. Subsequently, if the switch S is opened again, the integrated circuit by means of its inbuilt programs disconnects the motor means control and is thereafter rendered incapable of operating the motor again. The programming of an integrated circuit in this way may easily be carried out by programming specialists and does not therefore need to be described here in detail. According to other variations of the invention set out by dotted lines the switch S may be situated between the quartz Q and the circuit IC or between the circuit and the motor means 7 or yet again between the circuit and the battery B.

Figures 3, 7, 8, 9:
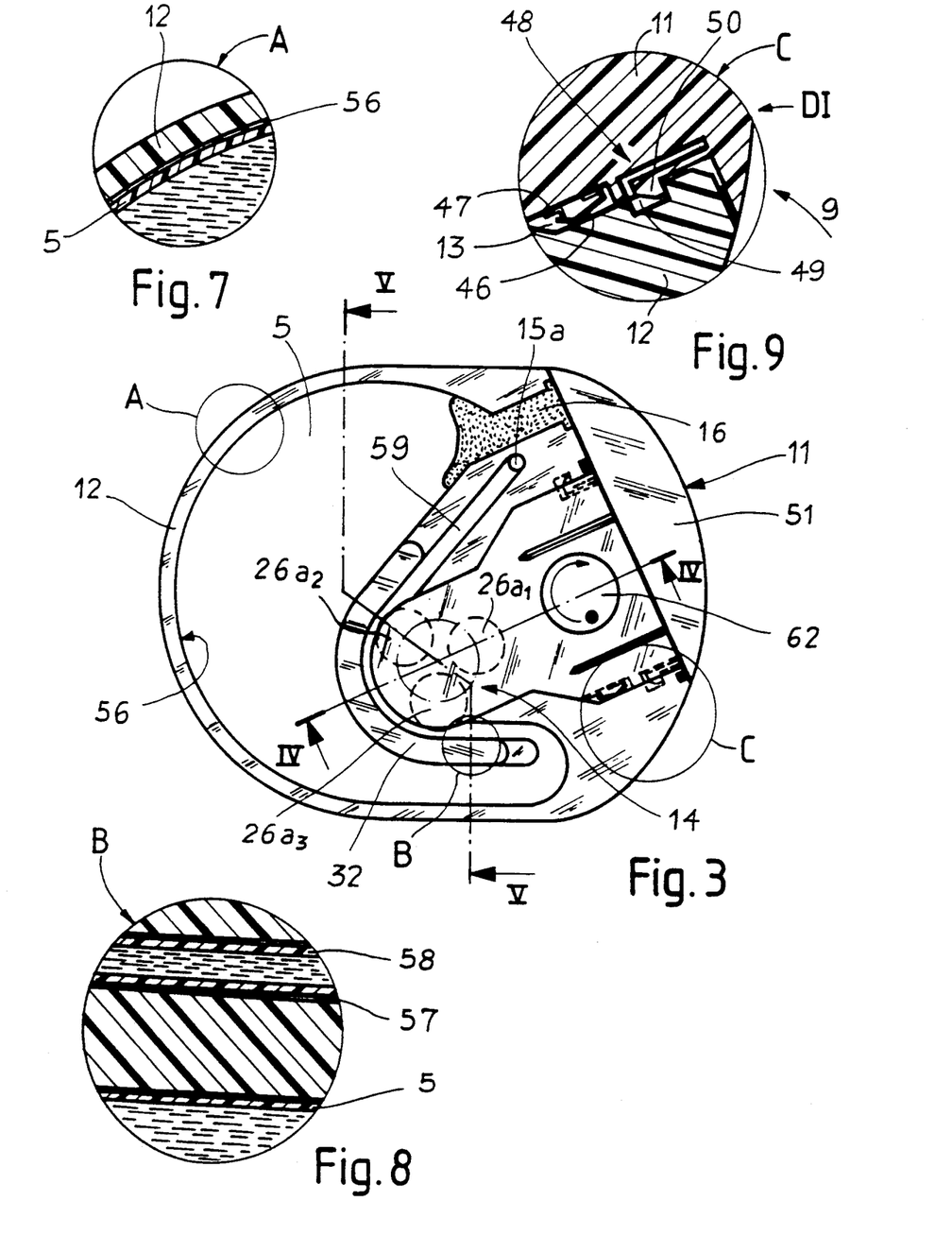

FIG. 9 illustrates a preferred embodiment of the invention for the electrical contact means 9. The movable contact of the switch S is here in the form of an elastic spring 46 fixed against the lateral wall of the motor module 11 and cooperating with a contact block 47 fixed adjacent thereto and forming the fixed contact of the switch S. It is thus readily apparent that the switch S in this form is closed when the module motor 11 is inserted into the cavity 13. The side wall of the latter thus fulfilling the function of the push button for the spring leaf 46.

FIG. 9 also shows the assembly means 48 for the modules 11 and 12 which are provided above the contact means 9 and slightly set back with respect to those in the direction of insertion DI of the module 11.

This assembly means comprises on the one hand two cavity 49 formed respectively in the side walls of the cavity 13 and on the other hand two elastic hooks made out of the same material as the body of the motor module 11, each hook hooking into one of the cavity 49 after complete insertion of the module 11 into the module 12.

It will be noted that if one attempts to remove the module 11 from the module 12 after a first assembly, the hooks 50 break which prevents any secure reassembly of the two modules.

As clearly shown in FIG. 2 the body 36 is provided with a gripping head 51 which is formed in one piece and which while facilitating manipulation of the motor module 11 completely covers the cavity 13. As a result of this, the cavity 13 is rendered completely inaccessible after assembly of the two modules, the filling orifice 16 is completely hidden and it is not possible to reach either the electrical contact means 9 or the assembly means 48.

In addition, a joint 52 surrounds the hole in the cavity 13 against which is applied the interior face of the gripping head 51, the spring nature of this joint ensuring preferably the positive hooking of the hooks 50 into the cavity 49 in a direction opposite to that of the arrow DI (FIG. 9).

Figure 11:
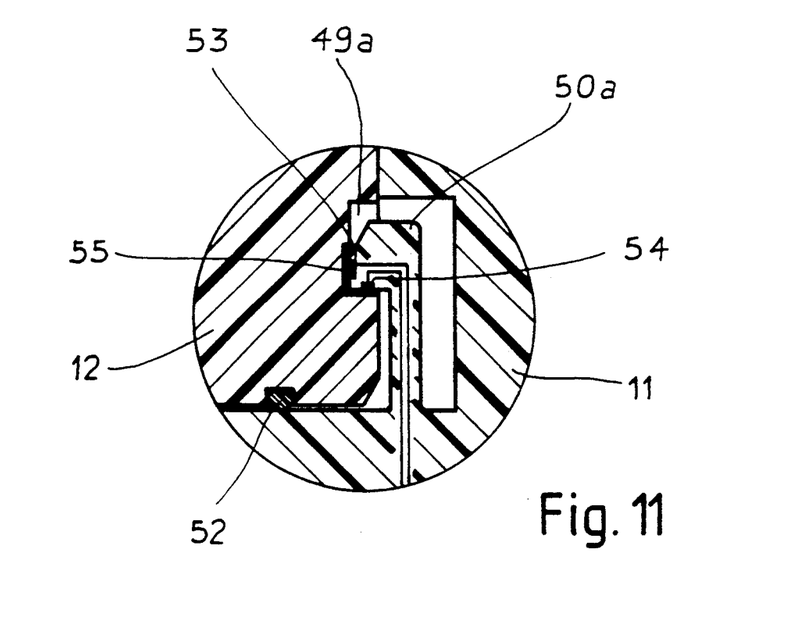
FIG. 11 shows a first variation of the way of making the electrical contact means and the assembly means represented in FIG. 9.

FIG. 11 illustrates a second embodiment of the electrical contacts and permanent disconnection means of the operation of the pump.

The motor module 11 is equipped at each side thereof with a hook 50a of a shape identical to that shown in FIG. 9. The supply reservoir module 12 is also provided with a recess 49a which attaches itself to the hook 50a.

One of the hooks 50a carries at its extremity two separate electrical contacts 53, 54 connected to the terminals of the integrated circuit IC according to the block diagram of FIG. 10 by connections which are not shown. This hook 50a thus constitutes a mechanical support element for the electrical contact means. At the bottom of the recess 49a there is provided a metallic continuous spring 55 and the shape of this hollow is so adapted that the contacts 53 and 54 can be connected together by the spring 55 when the modules are assembled and thus has the effect that the pump is put into operation.

As shown earlier in FIG. 9 the separation of the motor module and the supply module 12 results in breakage of the hook 50a and thus permanently disconnects operation of the pump since it is very difficult to refix the hook 50a and to re-establish the electrical connections to the integrated circuit IC.

This apparatus may constitute a second method for the permanent disconnection of the functioning of the pump which is not incompatible with programming of an integrated circuit as described above. However, with this embodiment of the invention one is also able to possibly dispense with programming the integrated circuit in a manner such that it automatically blocks after breakage of the connection made between the contacts 53 and 54 and the spring 55.

Figure 12:
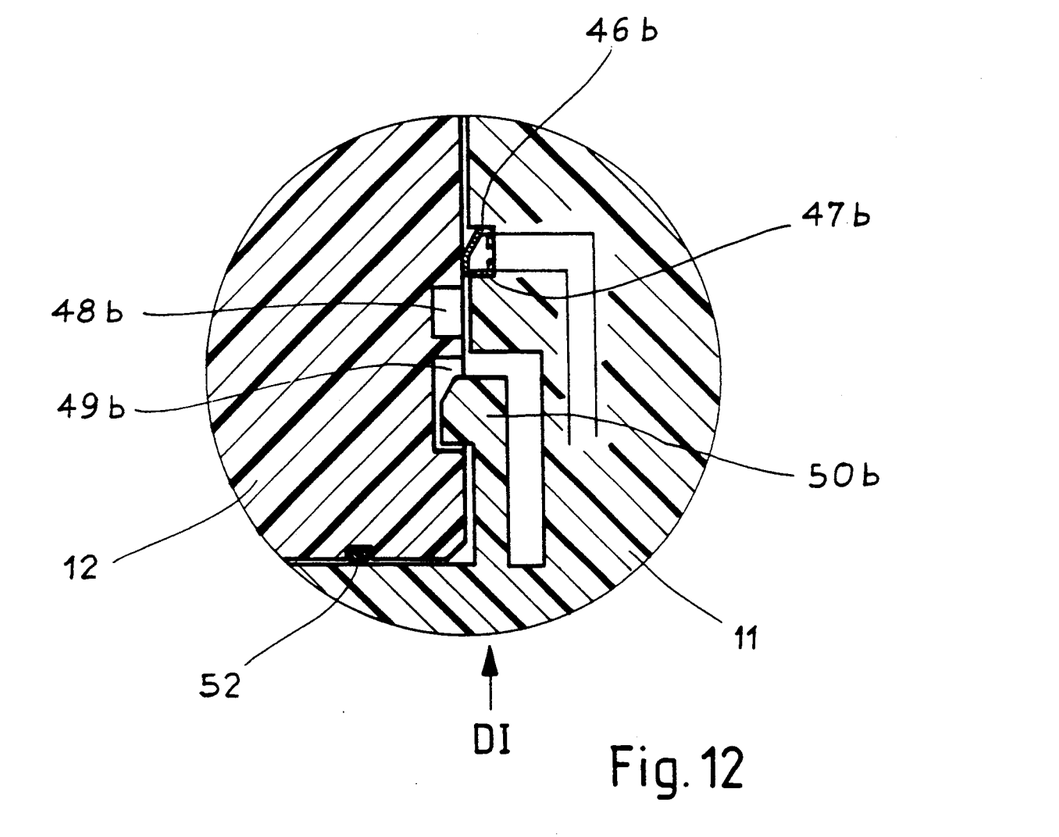
FIG. 12 shows a second variation of an embodiment of the electrical contact means and means for assembly represented in FIG. 9.

FIG. 12 illustrates a third embodiment of the electrical contact means and permanent disconnection means of the operation of the pump.

In a manner similar to that already described for FIG. 11 the motor module 11 is provided on each side thereof with a hook 50b and the supply reservoir is also provided on each side of the cavity 13 with a recess 49b adapted to engage with the said hook 50b. This hook 50b and the recess 49b have a configuration identical to those shown in FIG. 9

The movable contact of the switch S here takes the form of a conducting spring leaf 46b fixed to the side wall of the motor module 11 and cooperating with a contact block 47b fixed adjacent thereto and forming the fixed contact of the switch S. This spring 46b and contact block 47b are connected with the inlet terminals of the integrated circuit IC (not shown) according to the block diagram of FIG. 10. It can thus simply be seen that the switch S according to this plan is closed when the motor module 11 is inserted into the cavity 13 of the module 12 since the side wall of this cavity fulfils the function of the push button of the spring leaf 46b. But after assembly of the two modules 11 and 12, putting into operation is automatic. In addition the module 12 is provided with a second recess 48b set back slightly with respect to the spring 46b in the direction of insertion DI of the module 11.

If after assembly of the two modules attempts are made to remove the module 11 from the module 12 (direction opposite to that of DI), not only are the spring hooks 50b held by the recess 49b broken but the spring leaf 46b is forced aside in an outward direction on account of its shape and elasticity and is also broken in that it is held by the second recess 48b. The functioning of the pump is thus disrupted in a permanent manner since it is subsequently very difficult if not impossible to restick the spring 46b and to recreate the electrical connections leading to the circuit IC.

Finally, it should be noted that this third embodiment of the invention for the permanent connection of the operation of the pump is not incompatible with programming the integrated circuit described above.

In these three embodiments of the invention the electrical contact means and the permanent disconnection means for the operation of the pump, which have been described, it is clear that the features which have been described a being in the module 11 could be situated in the module 12 and vice versa.

There now follows a more detailed description of the reservoir module. As may be seen from FIGS. 2, 3, 7 and 8 the reservoir module 12 defines an area 56 in which is placed a reservoir 5 which comprises a bag of supple plastic material, for example PVC, covered by a seal (not shown). The preferred volume of the bag size is 10 cc corresponding to 8 cc of liquid to be injected (based on 1 cc/day for 8 days for example) and 2 cc in reserve. This volume is only given by way of example.

The housing 56 is extended at one of its extremities by a channel 57 (FIG. 8) enabling one to guide and hold a portion of the tube 58. This tube 58 connects the bag 5 with a Y-shaped connector 29 (FIG. 2).

In a similar manner, another channel 59 connects the tube (not shown) with a Y-shaped exit piece 30 to the exit 15a. These channels 57 and 59 are connected at the level of the end of the cavity 13 so that two tubes 28a and 28b may be pressed directly by the rotor 14 against the grooves 31a and 31b described above. In addition the bag 5 is equipped at the side opposite to that having the tube 58 with a septum arranged to the side of the cavity 13.

The pump is equipped with one or more audio and visual alarms which can indicate malfunctioning of the apparatus. These alarms will now be described in more detail.

As shown in FIGS. 4 and 10, the audio alarm comprises a vibrator 60 which is preferably disposed in an area 61 designed for this purpose in the cover plate 37 of the motor module 11 above the motor means 7. The vibrator 60 may also be disposed in the reservoir module 12 if it is more suitable to fit the audio alarm in that module. The alarm 60 may be connected to the terminals of the integrated circuit IC as soon as it detects the putting into operation of the pump, the end of operation, a motor failure or an obstruction in one of the tubes (28a, 28b). One may also equip the circuit IC with a circuit to detect the end of the life of the battery B or to sound the alarm 60 when the circuit is activated.

A visual alarm 62 may also be provided indicating malfunctioning or stopping of the rotor 14 or the motor means 7 (FIGS. 2 and 4). This alarm comprises a disk 63 of which the upper face has on its periphery a coloured point 64 being fixed on the minute hand 64a of the watch movement, this hand being coaxial with the hand 42. This latter passes the hole 65 provided in the body 36. In this way all variations in the rotation of the motor means 7 or the rotor 14 are converted by a corresponding variation in the speed rotation of the disk 63 or in its simply stopping.

So that the periphery of the disk 63 may be seen from the outside, the cover plate 37 of the motor module 11 and the reservoir module 12 itself are made in a transparent plastic material, the vibrator 60 covering the major part of the disk 64.

Nevertheless, if the vibrator 60 is placed in the module 12, the entire disk 63 becomes visible.

Finally, in order to avoid the motor module 11 being inserted the wrong way around into the reservoir module 12 one may for example provide on one of the faces of the motor module 11 longitudinal projections 66 which cooperate with longitudinal grooves 67 provided on the corresponding face of the cavity 13.

The functioning of the pump will now be described hereinafter.

If the pump is used in a hospital situation, the personnel carefully take one of the supply modules 11, unsterilized, and a sterilized module 12, packed separately. The medical staff first equip a patient with a pump according to the invention, then fill the appropriate medicament into the bag 5 with the aid of a syringe passing through the septum 16 until it is seen that the medicament is coming out of the exit 15a which serves to purge air contained therein from the pump. This purge is facilitated by the configuration of the bag 5.

The motor module 11 is then passed into the cavity 13 which has the following results,
 the pump is put into operation by way of the electrical contacts 9,
 the module 11 is firmly fixed in the module 12 by means of the hooks 50 which hook onto the recess 49.

It should be then understood that the pump is immediately thereafter placed on the patient with the aid of a hyperdermic syringe.

Having regard to FIG. 6 it will be seen that when the pump is put into operation the rotor 14 commences to turn, the rollers 26a and 26b press one after the other against the tubes 20a and 20b respectively by way of a progressive movement which results from the shape of the profile of the grooves 31a, 31b of the part 32. The tubes in the area situated between the rollers 26a, 26b may rest in the grooves 20a, 20b of the rotor 14. The separation by 60° between the rollers 26a and the rollers 26b enables a regular supply of medicament in the exit.

By way of example if the quartz Q employed in the control means 8 operates with a frequency of 32768 Hz, one may obtain by six divisions by two and a division by five a control frequency for the pumping motor (which is of the step type) of 102.4 Hz. The motor 41 being of the monophase bipolar type operates twice for each rotation which with an appropriate gear reduction formed by the wheel 44 and the crown 18 gives a speed to the rotor 14 of one rotation every 36 minutes. The average supply of the pump may thus be of the order of 1 cm$^3$ in 24 hours. By changing the internal diameter of the tubes 28a, 28b (but conserving the same thickness of the tube), one can also achieve a supply of around 3 cm$^3$ in 24 hours.

We claim:
1. A portable pump for the administration of a therapeutic liquid substance comprising the following features:
 a supply reservoir for the said substance;
 pumping means permitting provision of the said therapeutic substance from the supply reservoir up to the exit of said pumping means;
 motor means for setting into operation the said pump means;
 control means for the said motor means;
 said features being disposed in a plurality of assembled modules wherein two of the said modules include mating electrical contact means for setting said pump into operation upon assembly of the modules; and
 means actuable by the disassembly of said two modules for permanently and irreparably disabling said pump.

2. A portable pump according to claim 1 wherein said control means includes a integrated circuit and said permanent disabling means are incorporated into said integrated circuit.

3. A portable pump according to claim 2 wherein the integrated circuit includes means for stopping the operation of the motor means in a permanent manner when said electrical contact means is opened upon the disassembly of said two modules.

4. A portable pump according to claim 1 wherein said permanent disabling means include mechanical elements carrying said electrical contact means and wherein said mechanical elements are destroyed in a permanent manner when said two modules are disassembled.

5. A portable pump according to claim 1 wherein said electrical contact means are disposed in one of said two modules and said permanent disabling means comprise mechanical elements incorporated into the other of said two modules and wherein said mechanical elements destroy said electrical contact means in a permanent manner when said two modules are disassembled.

6. A portable pump according to claim 5 wherein said electrical contact means comprise a leaf spring and a contact block, and wherein said mechanical elements comprise a recess, said leaf spring being disposed in the said recess for being broken if the said modules are disassembled.

7. A portable pump according to claim 1 wherein the pump means, the motor means and the control means are provided in the modules incorporating the electrical contact means.

8. A portable pump according to claim 1 wherein said supply reservoir is disposed in one of said two modules and wherein said reservoir has a filling orifice inaccessibly disposed when the module is assembled with the other of said two modules.

9. A portable pump according to claim 1 wherein said control means comprises an integrated circuit, a quartz crystal oscillator connected to said integrated circuit a battery, and a disconnect formed by the electrical contact means.

10. A portable pump according to claim 9 wherein it comprises at least one audio alarm for the malfunctioning of the motor means and/or the rotor, this alarm comprising an integrated circuit and a vibrator connected to said integrated circuit.

11. A portable pump according to claim 10 wherein the integrated circuit comprises a circuit for the detection of the end of the battery life thereby activating a vibrator.

12. A portable pump according to claim 1 further comprising assembly means including at least one elastic hook provided on one of said two modules and by at least one recess provided in the other of said two modules with which it is assembled, the hook being disposed in said recess after complete insertion of one of the modules into the other.

13. A portable pump according to claim 12 wherein said permanent disabling means include mechanical elements carrying said electrical contact means and wherein said mechanical elements are destroyed in a permanent manner when said two modules are disassembled and wherein said elastic hook is connected with the mechanical elements carrying the electrical contact means.

14. A portable pump according to claim 1 wherein the pump means include a peristaltic pump comprising a rotor having a plurality of rollers disposed on one level, a toothed crown coupled to said motor means, a bearing member having a groove, a flexible tube disposed in said groove connecting said reservoir with said exit of said pumping means, said rollers pressing against the tubes at particular moving points.

15. A portable pump according to claim 14 wherein one of said two modules is a motor module containing a rotor, the motor means, the control means and the other of said two modules is a supply module having a supply reservoir, a filling orifice coupled to said supply reservoir, said tube and said bearing member.

16. A portable pump according to claim 15 including a second flexible tube connected in parallel with said first mentioned flexible tube, Y-connectors connecting the extremities of each of the tubes, thereby to form a joint exit from the supply reservoir and a communal exit of said pumping means, said rotor having a second plurality of rollers disposed on a second level coaxial with said first level, the rollers of the first level being angularly displaced with respect to the rollers of the second level in order to provide a regular supply of liquid from the exit of said pumping means.

17. A portable pump according to claim 15 wherein the supply module comprises a box equipped with a cavity at the bottom of which are disposed a bearing member and tubes and in that the motor module has a configuration essentially complementary to that of the cavity and is so configured that it can be introduced into the said cavity, the rotor being placed facing the tubes when the two modules are assembled.

18. A portable pump according to claim 15 having sealing means for sealing the pump means when the two modules are assembled.

19. A portable pump according to claim 1 wherein the module containing the supply reservoir is sterilizable before assembly with the other module.

20. A portable pump according to claim 1 wherein the reservoirs comprises a bag of supple sealed plastic material.

21. A portable pump according to claim 1 wherein it comprises at least one visual alarm means for the malfunctioning of the motor means, this alarm comprising a disk fixed to the arm at the exit of the motor means and being rotatably carried by the latter.

22. A portable pump according to claim 1 wherein the sealing means comprise a joint surrounding the cavity leading to the supply reservoir module.

* * * * *